(12) United States Patent
Rubin et al.

(10) Patent No.: US 10,238,341 B2
(45) Date of Patent: Mar. 26, 2019

(54) SYSTEMS AND METHODS FOR AUTONOMOUSLY SOOTHING BABIES

(71) Applicant: Graco Children's Products Inc., Atlanta, GA (US)

(72) Inventors: Zachary Rubin, Atlanta, GA (US); Bradley Keith Hondros, Atlanta, GA (US); Mubeen Ahmad, Atlanta, GA (US); William Andrew Steer, Cambridge (GB); Justin Pinkney, Cambridge (GB); Bart A. Smudde, Cumming, GA (US); Brian S. Kelly, Alpharetta, GA (US)

(73) Assignee: Graco Children's Products Inc., Atlanta, GA (US)

(*) Notice: Subject to any disclaimer, the term of this patent is extended or adjusted under 35 U.S.C. 154(b) by 0 days.

(21) Appl. No.: 15/602,831

(22) Filed: May 23, 2017

(65) Prior Publication Data

US 2017/0340285 A1  Nov. 30, 2017

Related U.S. Application Data

(60) Provisional application No. 62/340,725, filed on May 24, 2016.

(51) Int. Cl.
*A63H 33/00* (2006.01)
*A61B 5/00* (2006.01)
(Continued)

(52) U.S. Cl.
CPC .............. *A61B 5/6887* (2013.01); *A47D 9/02* (2013.01); *A61B 5/6891* (2013.01);
(Continued)

(58) Field of Classification Search
CPC .................................................... A63H 33/006
See application file for complete search history.

(56) References Cited

U.S. PATENT DOCUMENTS 4,181,813 A  1/1980 Marley
4,627,091 A  12/1986 Fedele
(Continued)

FOREIGN PATENT DOCUMENTS

CN  2595087 Y  12/2003
CN  2832126 Y  11/2006
(Continued)

OTHER PUBLICATIONS

Bandala et. al. "Modelling and characterization of an artifical neural network for infant cry recognition using mel-frequency cepstral coefficients" Jan. 29, 2015, IEEE, pp. 3-6 & 8-9.*
(Continued)

*Primary Examiner* — Gene Kim
*Assistant Examiner* — Alyssa Hylinski
(74) *Attorney, Agent, or Firm* — Eversheds Sutherland (US) LLP

(57) ABSTRACT

Systems and methods are disclosed for autonomously soothing babies. An example method may include receiving a first sound input from a microphone, processing the first sound input, determining a baby status based at least in part on the first sound input, determining an output action based at least in part on the baby status; and implementing the output action at the children's apparatus.

17 Claims, 6 Drawing Sheets

(51) Int. Cl.
    *A47D 9/02*     (2006.01)
    *B62B 9/22*     (2006.01)
(52) U.S. Cl.
    CPC ......... *A61B 5/7405* (2013.01); *A63H 33/006* (2013.01); *B62B 9/22* (2013.01); *A61B 5/4809* (2013.01); *A61B 2503/04* (2013.01)

(56) References Cited

U.S. PATENT DOCUMENTS

| | | |
|---|---|---|
| 5,452,274 A | 9/1995 | Thompson |
| 5,668,780 A | 9/1997 | Hsien |
| 5,873,062 A | 2/1999 | Hansen |
| 6,004,259 A | 12/1999 | Sedaros |
| 6,496,115 B2 | 12/2002 | Arakawa |
| 7,274,298 B2 | 9/2007 | Frank |
| 8,314,696 B2 | 11/2012 | Stut |
| 9,009,038 B2 | 4/2015 | Hong |
| 9,020,622 B2 | 4/2015 | Shoham |
| 9,247,346 B2 | 1/2016 | Kuo |
| 2002/0135485 A1 | 9/2002 | Arakawa |
| 2002/0167140 A1 | 11/2002 | Pike |
| 2003/0069079 A1* | 4/2003 | Kelly ............... A47D 13/105 472/119 |
| 2004/0130449 A1* | 7/2004 | Hung ............... A61M 21/00 340/573.1 |
| 2007/0058039 A1* | 3/2007 | Clark ............... A63H 33/006 348/143 |
| 2007/0200714 A1 | 8/2007 | Smith |
| 2008/0235030 A1 | 9/2008 | Sisto |
| 2008/0284409 A1 | 11/2008 | Barrera Vazquez |
| 2009/0062622 A1* | 3/2009 | Lin ............... A47D 9/02 600/300 |
| 2009/0128343 A1 | 5/2009 | Wu |
| 2011/0313555 A1 | 12/2011 | Shoham |
| 2013/0204617 A1 | 8/2013 | Kuo |
| 2013/0317815 A1* | 11/2013 | Hong ............... G10L 15/16 704/232 |
| 2014/0055263 A1 | 2/2014 | Witt |
| 2014/0250592 A1 | 9/2014 | Karp |
| 2014/0265480 A1 | 9/2014 | Perrin |
| 2015/0038072 A1 | 2/2015 | Cordier |
| 2015/0045608 A1 | 2/2015 | Karp |
| 2015/0105608 A1* | 4/2015 | Lipoma ............... A61B 5/6896 600/27 |
| 2015/0265206 A1* | 9/2015 | Sheinkopf ............... G10L 25/66 600/586 |
| 2015/0273698 A1* | 10/2015 | Bender ............... B25J 11/009 701/23 |
| 2015/0288877 A1* | 10/2015 | Glazer ............... H04N 5/2251 348/77 |
| 2016/0093281 A1 | 3/2016 | Kuo |
| 2016/0150338 A1 | 5/2016 | Kim |
| 2016/0165961 A1 | 6/2016 | Karp |
| 2016/0166081 A1 | 6/2016 | Karp |
| 2016/0174728 A1 | 6/2016 | Karp |
| 2016/0174841 A1 | 6/2016 | Proud |
| 2016/0183695 A1* | 6/2016 | Veron ............... A47D 9/00 340/573.1 |
| 2016/0293042 A1* | 10/2016 | Pradeep ............... A61B 5/002 |

FOREIGN PATENT DOCUMENTS

| | | |
|---|---|---|
| CN | 101057736 A | 10/2007 |
| CN | 101375791 A | 3/2009 |
| CN | 201274923 Y | 7/2009 |
| CN | 107224149 A | 10/2017 |
| CN | 107928250 A | 4/2018 |
| CN | 107951276 A | 4/2018 |
| JP | 2003337591 A | 11/2003 |
| WO | 2004/069319 A1 | 8/2004 |
| WO | 2016138441 A1 | 9/2016 |

OTHER PUBLICATIONS

Bandala et. al. "Modelling and characterization of an artifical neural network for infant cry regonition using mel-frequency cepstral coefficients" Jan. 29, 2015, IEEE, pp. 3-6 & 8-9.*

Bandala et.al. "Modelling and characterization of an artificial neural network for infant cry recognition using mel-frequency cepstral coefficients" Jan. 29, 2015, IEEE, pp. 3-6 & 8-9.*

Combined Search and Examination Report issued in United Kingdom Application No. GB1708214.0, dated Oct. 31, 2017 (7 pages).

* cited by examiner

Sound Input and Device Output Table 200

| Baby Status | Adjust Swing Speed? | Adjust Sound? | Adjust Vibration? |
|---|---|---|---|
| Crying | Yes | Yes | Yes |
| Whining | Yes | Yes | No |
| Babbling | No | No | No |
| Laughing | No | No | No |
| Non-Baby Noise | No | No | No |
| ... | ... | ... | ... |

FIG. 2

SYSTEMS AND METHODS FOR AUTONOMOUSLY SOOTHING BABIES

CROSS-REFERENCE TO RELATED APPLICATIONS

This application claims the benefit of U.S. Provisional Application No. 62/340,725, filed May 24, 2016, the entirety of which is hereby incorporated by reference.

BACKGROUND

Children's products may be used to soothe children, such as babies. For example, motorized swings, bouncers, and the like may provide entertainment for babies. However, children's products may be unable to monitor a baby's status, and may therefore be unable to react to a change in a baby's status. For example, a motorized swing may be unable to monitor whether a baby has fallen asleep, and may therefore be unable to change, in one example, a swing speed as a result of the baby falling asleep.

SUMMARY

According to an embodiment of the disclosure, an example method may include receiving a first sound input, determining a Fourier transform of the first sound input, determining a standard deviation of the Fourier transform, determining a baby status based at least in part on the standard deviation, and determining an output action based at least in part on the baby status.

According to an embodiment of the disclosure, an example apparatus may include a baby supporting portion, or a portion configured to support and/or receive a baby or child, such as a baby seat, a child play area, etc. and one or more processor(s) configured to execute computer-executable instructions to receive a first sound input, determine a Fourier transform of the first sound input, determine a standard deviation of the Fourier transform, determine a baby status based at least in part on the standard deviation, and determine an output action based at least in part on the baby status.

Other features and aspects of an apparatus for autonomously soothing babies, and manufacturing processes thereof, will be apparent or will become apparent to one with ordinary skill in the art upon examination of the following figures and the detailed description. All other features and aspects, as well as other system, method, and assembly embodiments, are intended to be included within the description and are intended to be within the scope of the accompanying claims.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIG. 2 schematically depicts an example sound input and device output table in accordance with one or more embodiments of the disclosure.

DETAILED DESCRIPTION

Embodiments of this disclosure relate to autonomous baby soothing systems and methods that may sooth children and babies by reacting to a child or baby's current status. For example, a baby's current status may be crying, laughing, alert, sleeping, or another status. Certain embodiments may determine a child or baby status by monitoring sound and/or motion produced by a child or baby in real-time. Upon determining a child or baby status, embodiments of the disclosure may determine one or more response or output actions. For example, if a baby is crying, a swing or rocking speed of a children's apparatus, such as a swing, bouncer, crib, playpen, rocker, playard, bassinet, sleeper, or jumper, or other children's apparatus, may be increased or decreased. In another example a sound volume (e.g., music, jungle, etc.) may be increased or decreased, or a vibration setting for generating a vibration of the children's apparatus may be increased or decreased. In some embodiments, more than one response or output action may be initiated based at least in part on the baby's status, as determined by the sound output from the baby. Embodiments of the disclosure may soothe children or babies autonomously, or without manual input. Certain embodiments of the disclosure may include motion sensing capabilities, including, in one example, accelerometer or motion sensors that detect a child's motion, which may be used independently or in conjunction with sound detection to determine a current baby status, and a response action. Some embodiments may determine that a child has been soothed or has fallen asleep, and as a result, may automatically modify or adjust one or more device settings. For example, after a child is determined to have fallen asleep (e.g., minimal or no sound or motion detected for a predetermined length of time, etc.), the device may gradually reduce a swing speed, reduce a light output or frequency, reduce a vibration level, and/or reduce a music or sound volume, including turning one or more of the preceding off.

Figure 1:
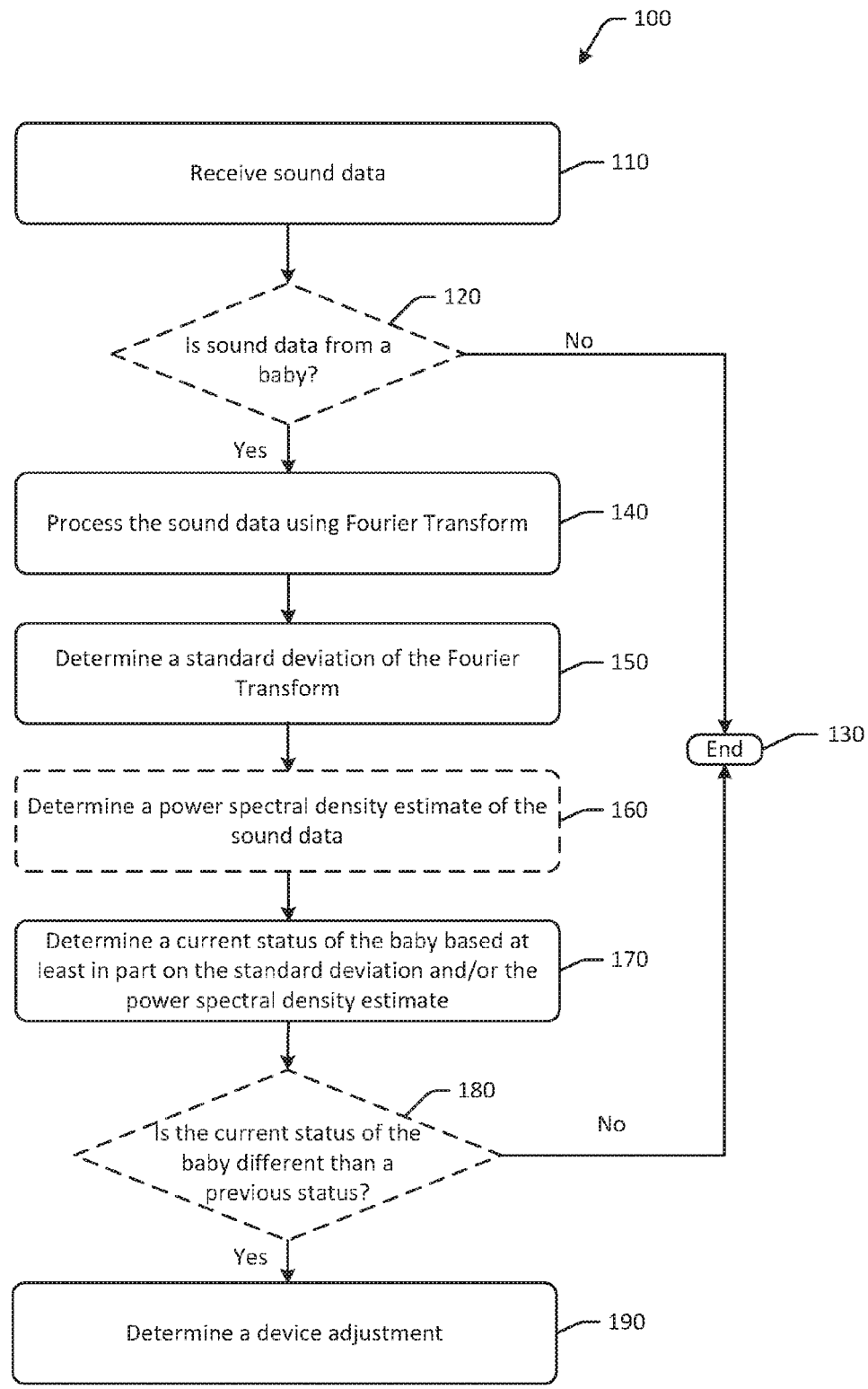
FIG. 1 schematically depicts an example process flow for autonomously soothing babies in accordance with one or more embodiments of the disclosure.

Referring to FIG. 1, an example process flow 100 for autonomously soothing babies in accordance with one or more embodiments of the disclosure is depicted. Example embodiments may include children's apparatuses or other baby devices that can include vibration motors, speakers, microphones, light sources, and other apparatuses. In some embodiments the microphone(s) may be noise-canceling. Other forms of children's apparatuses may be substituted herein for the swing apparatus, including, but not limited to a crib apparatus, a bouncer apparatus, a rocker apparatus, a playpen apparatus, a playard apparatus, a bassinet apparatus, a sleeper apparatus, or a jumper apparatus.

Block 110 of the process flow 100 includes receiving sound data. For example, a children's apparatus may include one or more microphones attached to a processor(s) or other electronics module (e.g., printed circuit board, etc.). In some embodiments, microphones may be positioned physically distant from a speaker or other audio source on the children's apparatus, so as to reduce signal interference in detected audio or sounds emitted from a child in the device. Sound data may be segmented, for example as discrete segments of sound having a predetermined length (e.g., 7 seconds, 10 seconds, etc.), or may be continuous, such as via an audio stream.

At optional determination block 120, a determination is made as to whether the sound data or audio signal is from a baby. Sound data may be digital data, while an audio signal may be an analog signal. In one example, the sound data or audio signal may be processed to determine a source of the sound data or audio signal. Processing may include performing one or more mathematical operations on the sound data or audio signal, including, but not limited to, frequency-domain analysis, Fourier transform, Welch's method (e.g., power v. frequency plotting, power spectral density estimation, etc.), standard deviation on data sets, data normalization, maximum and/or minimum value analysis (e.g., frequency, amplitude, etc.), and the like. Outputs from the processing of the sound data or audio signal may be compared to one or more data tables to determine whether the outputs correspond to expected values of sound generated by a baby. Audio signals or sound data may be processed to reduce signal noise, including noises generated by motion or vibration of the children's apparatus, speakers of the children's apparatus, and/or an ambient environment.

If it is determined that the sound data or audio signal was not generated by a baby, the process flow 100 may end at block 130. If it is determined that the sound data or audio signal was generated by a baby, the process flow 100 may proceed to block 140, at which the sound data or audio signal is processed using Fourier transform. In some embodiments, the Fourier transform may be determined during the determination at block 120.

At block 150, a standard deviation of the Fourier transform is determined. At optional block 160, a power spectral density estimate of the sound data is determined. In some embodiments, the power spectral density estimate may be determined during the determination at block 120.

At block 170, a current status of the baby is determined based at least in part on the standard deviation and/or the power spectral density estimate. For example, values of the standard deviation and/or a maximum output of the power spectral density estimate may be compared to one or more thresholds stored in a table, such as the table of FIG. 2. The thresholds may be associated with one or more baby statuses. In one example, a standard deviation may be between a range of 29 and 75 for sound produced by babies, with ranges of values between 29 and 75 associated with particular baby statuses. In some embodiments, a value of 29-45 may be associated with a crying baby status. Other thresholds may be associated with a maximum output of the power spectral density estimate determination. For example, maximum values between 4 and 8 may be associated with sound produced by babies, with certain ranges associated with particular baby statuses.

At optional determination block 180, a determination is made as to whether the current status of the baby is different than a previous status. Accordingly, changes is baby status may be determined. If it is determined that there is no change in baby status, the process flow 100 may proceed to end at block 130.

If there is a change in baby status, the process flow 100 may proceed to block 190, at which a device adjustment is determined. Device adjustments may be adjustments to one or more children's apparatus settings, and may be determined via one or more tables, with certain adjustments or output actions associated with particular baby statuses. For example, device adjustments may include vibration setting adjustments, swing speed adjustments, music or other sound volume adjustments, and the like.

In some embodiments, sound data and/or noise detection may be combined with other types of sensing what the baby is doing, such as motion sensing. For example, a baby may be crying and moving at the same time. An amount of movement may be determined prior to imparting a response action (e.g., swinging, vibration, etc.) or a device setting adjustment.

FIG. 2 schematically depicts an example sound input and device output table 200 in accordance with one or more embodiments of the disclosure. The sound input and device output table 200 may include one or more baby statuses associated with one or more output actions. For example, a baby status of crying may be associated with an adjustment of a swing speed, an adjustment of sound, and an adjustment of vibration. Other embodiments may include the adjustment of additional features, such as lights, music, rocking modes, and other features. Adjustments may include increasing level or frequency, decreasing level or frequency, starting, stopping, or another adjustment. A baby status of whining may be associated with an adjustment of a swing speed and an adjustment of sound. Baby statuses of babbling or laughing may indicate that the baby does not need to be soothed, and may therefore not be associated with any device adjustments. In some embodiments, babbling, laughing, and other baby statuses may be associated with different device adjustments that are based at least in part on a mode or a goal of the device. Similarly, non-baby noise may not be associated with any device adjustments. Other embodiments may include additional information, such as sound data values associated with particular baby statuses, specific device adjustments (e.g., increase volume 2 notches, etc.), and other data.

Figure 3:
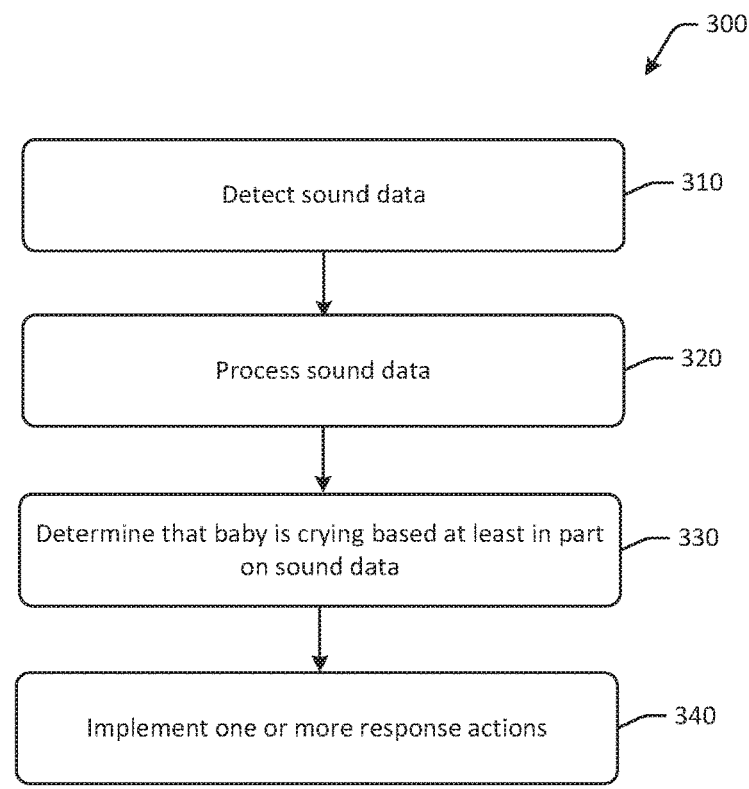
FIG. 3 schematically depicts an example process flow for autonomously soothing babies in accordance with one or more embodiments of the disclosure.

FIG. 3 depicts an example process flow 300 for autonomously soothing babies in accordance with one or more embodiments of the disclosure. A powered children's apparatus, such as a baby swing or other device, may be configured to detect and process sound in order to recognize a baby's cry, or another sign of distress, and autonomously implement one or more response actions to calm the baby. At a first block 310, a children's apparatus may be configured to detect sound. For example, the children's apparatus may include a microphone configured to capture ambient noise and generate an audio signal. Sound may be captured in discrete segments, such as segments of about 0.2 seconds, 0.5 seconds, 1.0 seconds, or other segment lengths, and processed thereafter.

At block 320, the detected sound may be processed. Sound may be detected by the device and processed in order to detect an acoustic signature of a baby's cry or other sign of distress. Sound processing may account for background noises, such as that of people talking, television or radio sounds, or other ambient noise detected along with sound emitted from a baby.

At block 330, the children's apparatus may determine that the baby is crying based at least in part on the detected sound. Embodiments of the disclosure may distinguish between multiple sounds emitted from a baby. For example, a babbling sound may be distinguished from a cry. Certain embodiments may implement machine learning techniques to process and classify audio signals.

At block 340, one or more response actions may be implemented. Response actions may include, for example, one or more adjustments to a speed or direction of the children's apparatus, an adjustment to a volume and/or type of music or sound, and/or an adjustment to a motion of the device (e.g., switch from vibration to rocking, etc.).

Figure 4:
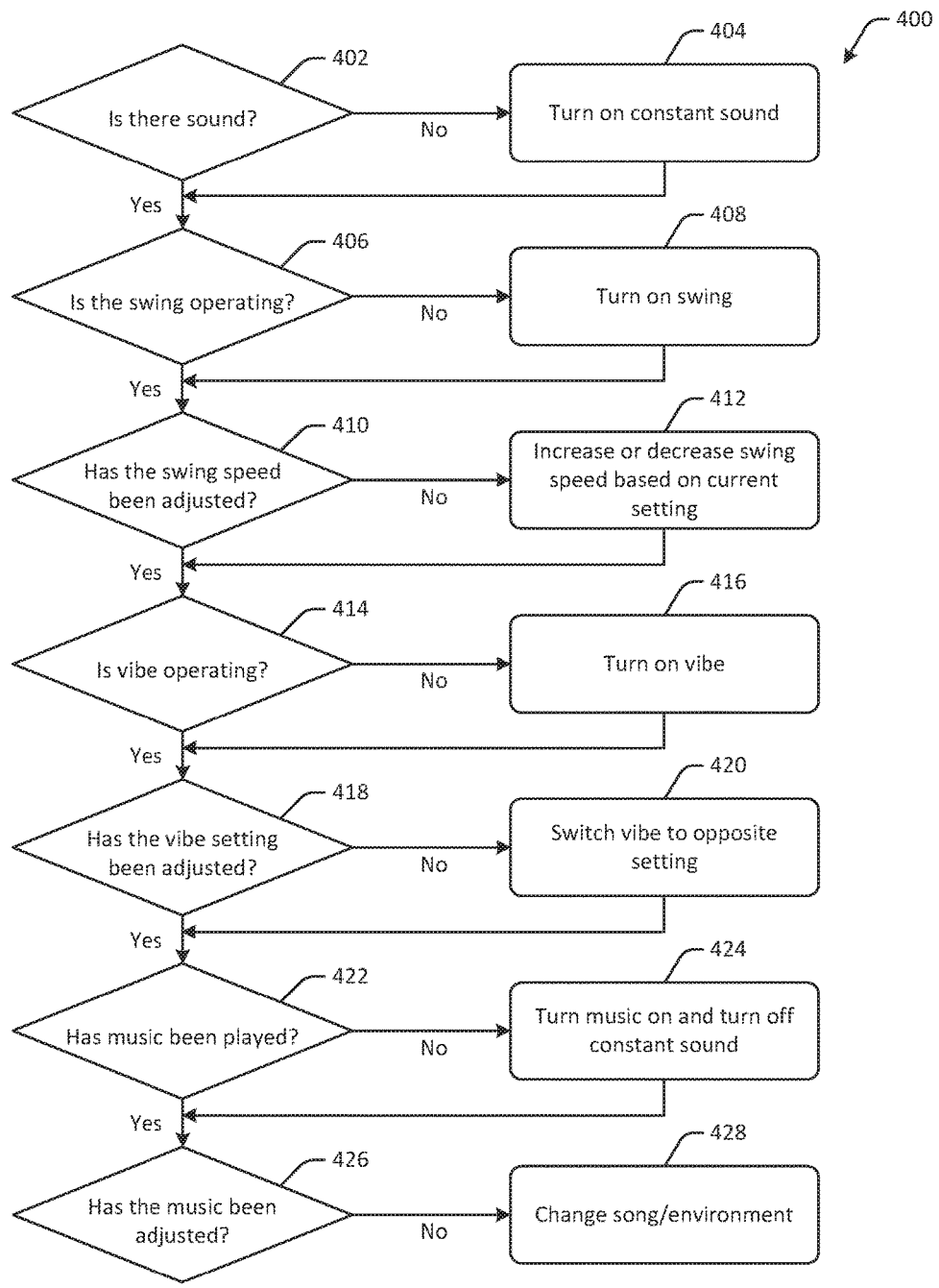
FIG. 4 schematically depicts an example response action hierarchy in accordance with one or more embodiments of the disclosure.

FIG. 4 depicts an example process flow of a hierarchy 400 of options to autonomously soothe babies in accordance with one or more embodiments of the disclosure. Infant distress may be caused for a number of reasons, and as a result, certain response actions may be effective for certain situations, while other response actions may be effective generally. For example, if an infant is in physical pain, a light massage may be an effective response action, whereas if an infant is generally unrestful, a light massage may not be as effective as, for example, a calming, constant sounds (e.g., white noise, heartbeat, etc.). The example hierarchy may be implemented in any suitable children's apparatus, such as a swing, a bassinet, a device with a swaddling insert, or another device.

In some embodiments, a hierarchy of response actions may be implemented in a preset or a custom order until the baby is no longer crying or unrestful. At a first determination block 402 in the hierarchy 400, a determination may be made as to whether a sound is playing. Sound may be a constant sound, such as a heartbeat, jungle sounds, or white noise, for example. If there is no sound, a first response action 404 in the hierarchy 400 may be to initiate or turn on a constant sound. After the sound is initiated, a predetermined time period may elapse, such as about 10 seconds, and a determination may be made as to whether the baby has stopped crying.

If the baby is still crying or otherwise not soothed, or if the sound was already playing, the hierarchy 400 may proceed to a second determination block 406, at which a determination is made as to whether a swing is operating. For devices without swings, the hierarchy may not include this determination block. If the swing is not operating, a second response action 408 may be to turn on the swing. A time period may be allowed to elapse before determining whether the baby has stopped crying after the swing is initiated.

If the baby is still crying or otherwise not soothed, or if the swing of the children's apparatus was already operating, the hierarchy 400 may proceed to a third determination block 410, at which a determination is made as to whether a swing speed has been adjusted. If the swing speed has not been adjusted, an adjustment to the swing speed may be made as a third response action 412. The swing speed may be increased or decreased depending on a current setting of the swing speed. For example, if the swing speed is at a maximum setting, the swing speed may be decreased, whereas if the swing speed is at a minimum setting, the swing speed may be increased. A time period may be allowed to elapse before determining whether the baby has stopped crying after the swing speed is adjusted. The constant sound, swing, and swing speed may be linked to one another as response actions in some embodiments.

If the baby is still crying or otherwise not soothed, or if the swing speed has already been adjusted, the hierarchy 400 may proceed to a fourth determination block 414, at which a determination is made as to whether a vibe is operating. Vibe may be a vibration setting that vibrates an area of the apparatus that supports the child. If the vibe is not operating, the vibe may be initiated as a fourth response action 416. The vibe may be set to a predetermined initial setting. A time period may be allowed to elapse before determining whether the baby has stopped crying after the vibe is initiated.

If the baby is still crying or otherwise not soothed, or if the vibe is already operating, the hierarchy 400 may proceed to a fifth determination block 418, at which a determination is made as to whether a vibe setting has been adjusted. If the vibe setting has not been adjusted, the vibe setting may be switched to an opposite setting as a fifth response action 420. A time period may be allowed to elapse before determining whether the baby has stopped crying after the vibe setting is switched.

If the baby is still crying or otherwise not soothed, or if the vibe setting has already been adjusted, the hierarchy 400 may proceed to a sixth determination block 422, at which a determination is made as to whether music has been played. If music has not been played, music may be turned on and the constant sound may be turned off as a sixth response action 424. A time period may be allowed to elapse before determining whether the baby has stopped crying after the music is turned on. A music volume may be set based at least in part on a loudness or volume of a baby's cry. For example, the music volume may be set to match the loudness of the baby's cry.

If the baby is still crying or otherwise not soothed, or if music has already been played, the hierarchy 400 may proceed to a seventh determination block 426, at which a determination is made as to whether the music has been changed. If the music has not been changed, the song or environment may be changed as a seventh response action 428. A time period may be allowed to elapse before determining whether the baby has stopped crying after the music is changed. The music may continue to change after predetermined time periods if the baby is still crying.

In some embodiments, if all soothing features of a device are powered on, then swinging speed may be adjusted, followed by sound, followed by vibe level. Certain embodiments may include additional features, such as recline adjustments that allow for babies to sit in an upright position, swaddling, light shows, flashing lights, toy mobiles, and pacifier options, as well as other features that can be manipulated for a particular device.

Certain embodiments may be configured to allow parents to preset favorite soothing options in a particular order, which may be used as the hierarchy to soothe a particular baby. Further, some embodiments may be configured to adjust a hierarchy based on input from a parent regarding preferred soothing techniques. For example, a parent may prefer music to be played before adjusting a swing speed, and may indicate that music is preferred by providing one or more inputs (e.g., a "like" button) to the device. Similarly, disliked response actions may be indicated to the device and moved further down the hierarchy. An amount of time between response actions (e.g., sound, vibe, etc.) may also be customized, in addition to particular response and order. For example, a parent may adjust a time interval before a subsequent response action to be 15 seconds, 30 seconds, or another time interval.

Figure 5:
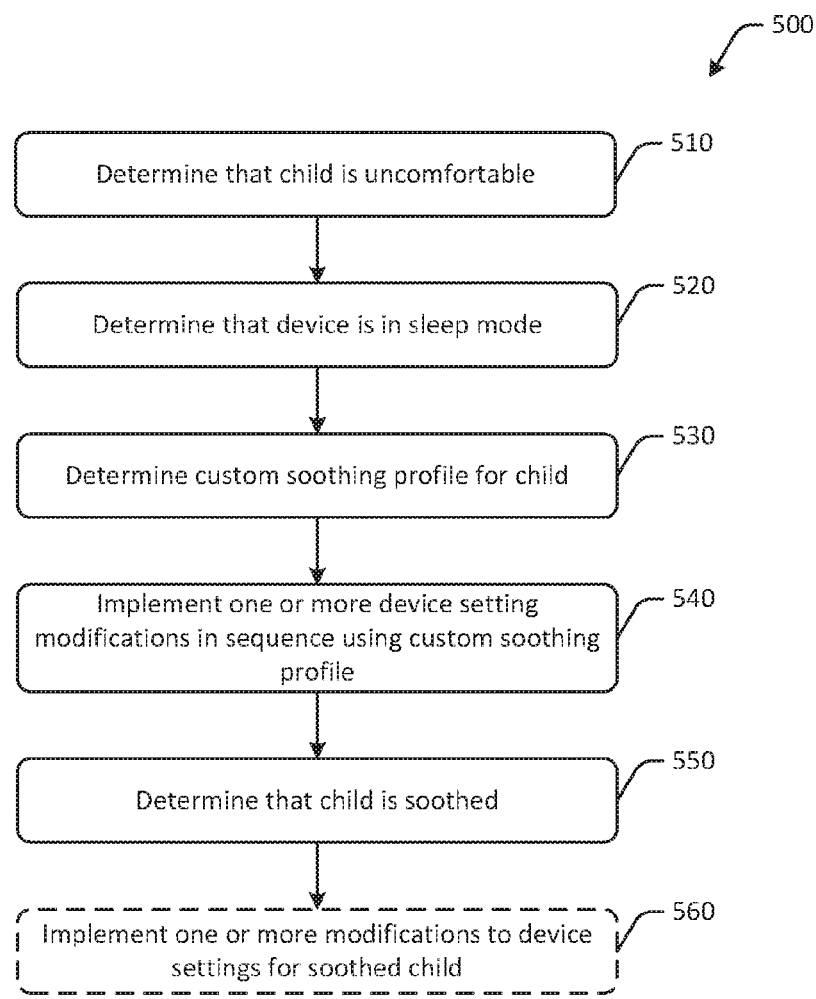
FIG. 5 schematically depicts an example process flow for using a custom soothing profile to autonomously soothe a child in accordance with one or more embodiments of the disclosure.

FIG. 5 depicts an example process flow 500 for using a custom soothing profile to autonomously soothe a child in accordance with one or more embodiments of the disclosure. The process flow 500 may be executed by one or more controllers or processors at a children's apparatus, while in some embodiments, some or all of the operations of FIG. 5 may be performed by a device in wired or wireless communication with the children's apparatus, such as a smartphone, a remote server, or another device. One or more of the operations of FIG. 5 may be performed at the processor(s). In some embodiments, the operations of FIG. 5 may be performed in a different order or may include additional or fewer operations.

At block 510 of the process flow 500, it may be determined that a child is uncomfortable. For example, a child may be positioned in a children's apparatus, such as a swing or rocker, and may be crying. Based at least in part on sounds and/or motion from the child, a determination may be made that the child is uncomfortable. Sounds may be captured using a microphone that is a part of the baby device and may be determined and/or processed locally at a processor(s) communicatively coupled to the microphone or at a wirelessly connected device.

At block 520, it may be determined that the baby device is in sleep mode. For example, the children's apparatus may have one or more modes or settings that can be initiated physically (e.g., using a switch, a button, a touchpad, etc.) or digitally (e.g., using a mobile application on a mobile device, etc.). Device modes may indicate a goal for the children's apparatus. For example, a sleep mode may indicate that the child in the children's apparatus is to be put to sleep, while a play mode may indicate that the child is not to be put to sleep. Other modes or different modes may be included.

Device modes may be associated with different profiles, such as a "parent" profile, which may include one or more personalized settings particular to the parent or child, and/or a "default" profile that may include a predetermined sequence of operations for various modes, and other profiles. In some embodiments, parent and default profiles may be different for specific goals or modes. For example, a play mode may be associated with a first parent profile, while a sleep mode may be associated with a second parent profile.

At block 530, a custom soothing profile for the child may be determined. For example, the sleep mode may be associated with a parent profile. The parent profile may include one or more device adjustments and/or a particular sequence of adjustments that are to be implemented at the children's apparatus in order to soothe a particular child. The parent profile may be a custom soothing profile that is input by and/or managed by a parent of the child to be positioned in or on the baby device. In some embodiments, a default profile may include a predetermined sequence of operations, such as adjustments to lights, sounds, motion, vibration, and other settings on the baby device that can be used to soothe the child. In some embodiments, machine learning may be used to modify and/or adapt the default profile or another profile over time based at least in part on the effectiveness of certain adjustments to the child at the children's apparatus. For example, if the child is determined to react better or otherwise be soothed by vibration rather than sounds, the default profile may be modified automatically to rank a vibration adjustment ahead of a sound adjustment when the child is to be soothed and/or the baby device is in sleep mode. Response actions that are determined to be more effective than others (e.g., as determined by length of time before the child is soothed, etc.) may be prioritized, as such actions may reduce a total length of time to sooth the child in the baby device.

At block 540, one or more device setting modifications may be implemented in the sequence defined by the custom soothing profile. For example, the parent may have a specific sequence of device setting modifications that are to be implemented at the children's apparatus when the children's apparatus is in sleep mode and the child is uncomfortable. The sequence may include, in one example, initiating vibration, adjusting vibration, initiating sound, initiating rocking motion, initiating light output, and the like. In one example, the custom soothing profile may be an active device setting modification profile, or a profile that is to be used for soothing the child. A user of the baby device may change the active profile to the default profile in some instances.

At block 550, it may be determined that the child is soothed. For example, inputs received at the microphone on the baby device may be analyzed by the processor(s) to determine that the child has stopped making a crying sound or other indications of discomfort for a predetermined length of time. In one example, the predetermined length of time may be a period of two minutes. Based on that information, the processor(s) of the baby device may determine that the child has been soothed.

At optional block 560, one or more modifications to the device settings of the baby device may be implemented for the soothed child. For example, once the processor(s) determines that the child is asleep or soothed for a predetermined length of time, device settings at the baby device may be modified. Post-soothing device setting modifications may include reducing an amount of vibration or swing speed, reducing sound or music volume, reducing light output or frequency, and/or turning one or more of the device settings to an off power mode, and other modifications.

Figure 6:
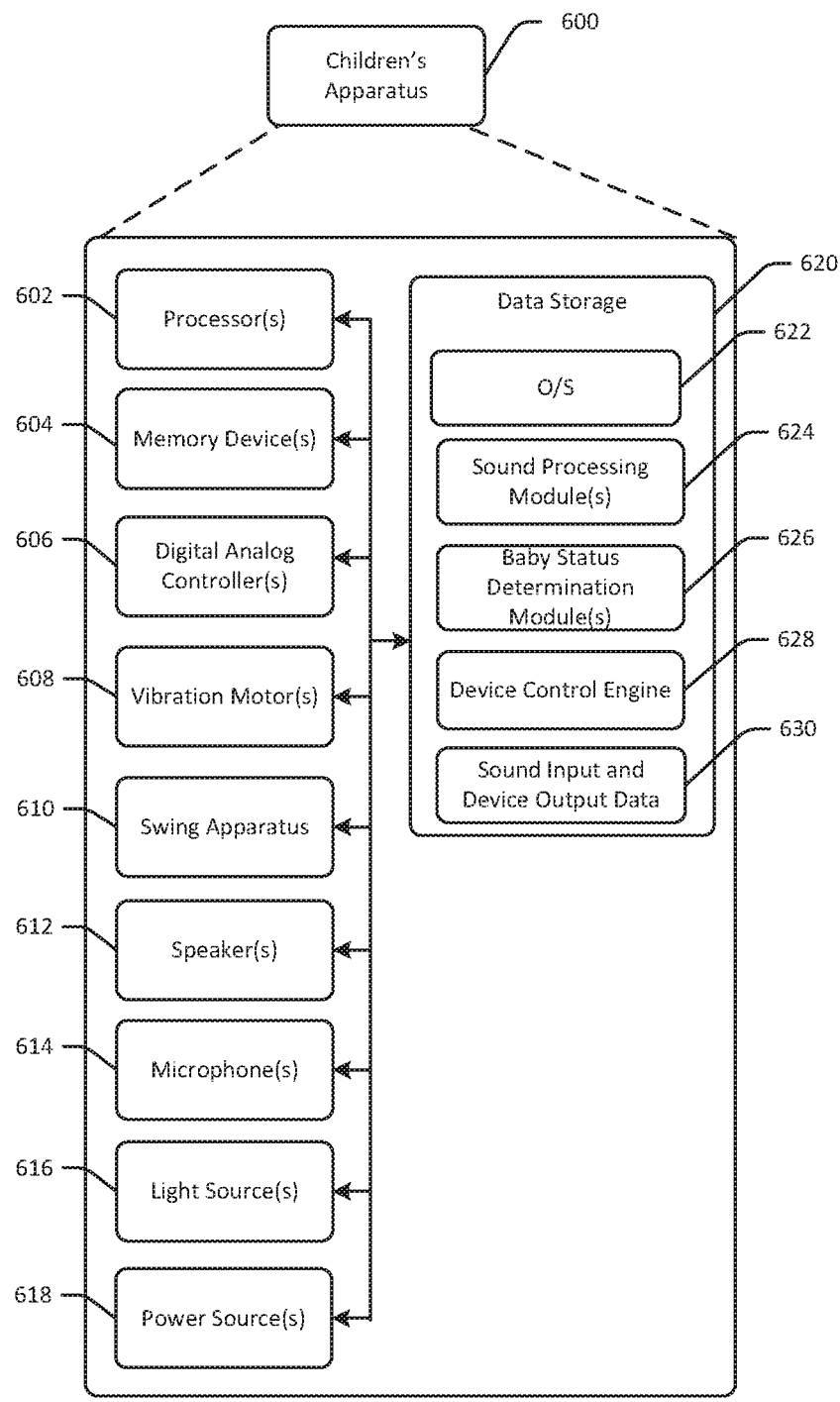
FIG. 6 schematically depicts an example autonomous baby soothing apparatus in accordance with one or more embodiments of the disclosure.

FIG. 6 schematically depicts an example autonomous children's apparatus 600 in accordance with one or more embodiments of the disclosure. The device 600 may be any suitable children's apparatus or children's product, such as one or more of a swing, a crib, a playpen, a rocker, a playard, a bouncer, a sleeper, a bassinet, a jumper, and other children's products that assist in soothing a child occupant of the product.

The children's apparatus 600 may include one or more processors 602 or controllers that control one or more aspects of the device 600. For example, the processor(s) 602 may receive sound data, generate music and/or sounds, control device settings, such as turning a vibration motor on/off in a predetermined or desired pattern, turning a nightlight, LED lights, or other such lights on/off in a desired or predetermined pattern, and other aspects of the device 600. Sounds may include white noise, music, jungle sounds, and the like.

The children's apparatus 600 may include one or more memory devices 604 that may store data, such as the table of FIG. 2, as well as sound or music data and data storage 620. The children's apparatus 600 may include one or more digital-to-analog converters 606 used to convert digital data to an analog signal.

The children's apparatus 600 may include one or more vibration motors 608, one or more swing apparatuses 610, one or more speakers 612, one or more microphones 614, one or more light sources 616, and one or more power sources 618. One or more components of the children's apparatus 600 may be connected to and powered by the power source 618. In some embodiments, one or more of the components may be coupled to the children's apparatus 600, while in other embodiments, one or more of the components may be distributed and/or in wired or wireless communication with the children's apparatus 600.

The vibration motor 608 may be housed under a seat, play surface, sleeping surface, or other child contacting surface on the baby soothing device 600, and may be configured to generate a vibration. A vibration intensity may be adjustable.

Vibration motors 608 may be direct current motors with offset or out-of-balance weights. The vibration motors 608 may include one or more solenoids with weights that may generate movement through one axis rather than two axes to produce a physical motion or vibration detectable by the child. For example, solenoids may be used to simulate a mother patting the child's back (such as to simulate burping or a soothing pat, etc.).

The swing apparatus 610 may include a swing motor configured to swing, for example, a baby seat or other baby carrier in a back and forth, side-to-side, elliptical, random, or circular motion. The speakers 612 may be configured to output sound at varying intensity and/or volume. The microphones 614 may be configured to receive ambient sound input at the children's apparatus 600 and generate sound data and/or analog signals as a result of ambient sound input. The light sources 616 may be any suitable light source, such as light emitting diodes or other light sources, and may be used to assist in soothing a child. In one example, one or more of the light sources 616 can be synchronized to turn on and off at preset times with the music and/or sound emitted by the speakers 612 to create a multi-sensory event.

The children's apparatus 600 may include the data storage 620. The data storage 620 may include an operating system 622 that may be in the form of software/firmware. The data storage 620 may include one or more sound processing module(s) 624, one or more baby status determination module(s) 626, one or more device control engine(s) 628, sound input and device output data 630, and one or more hierarchy determination module(s) 632.

The sound processing module(s) 624 may be configured to receive sound data and to process the sound data using one or more functions. The baby status determination module(s) 626 may determine a baby status based at least in part on outputs from the sound processing module(s) 624 and/or the sound input and device output data 630. The device control engine(s) 628 may be configured to control one or more components of the device 600 based at least in part on a baby status and associated device actions. The sound input and device output data 630 may include one or more device actions associated with one or more baby statuses. The one or more hierarchy determination module(s) 632 may be configured to implement and/or modify one or more soothing response action hierarchies that provide an order of implementation to soothe a baby.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method comprising:
   receiving, by a children's apparatus comprising one or more computer processors coupled to at least one memory, a first sound input from a microphone;
   processing the first sound input comprising:
      determining a Fourier transform of the first sound input; and
      determining a standard deviation of the Fourier transform;
   determining a baby status based at least in part on the standard deviation of the Fourier transform;
   determining an output action based at least in part on the baby status; and
   implementing the output action at the children's apparatus.

2. The method of claim 1, wherein processing the first sound input further comprises detecting an acoustic signature of a baby's cry using a sound processing algorithm.

3. The method of claim 2, wherein the sound processing algorithm comprises a mel frequency cepstral coefficient sound processing algorithm.

4. The method of claim 1, further comprising:
   determining a power spectral density estimate of the first sound input; and
   determining a maximum value of the power spectral density estimate;
   determining that the standard deviation and the maximum value are associated with the output action;
   wherein determining the baby status is based at least in part on the maximum value.

5. The method of claim 1, wherein the baby status is an uncomfortable baby status, the method further comprising:
   determining an operational mode of the device; and
   determining an active device setting modification profile using the operational mode;
   wherein determining the output action comprises selecting an output action using the active device setting modification profile.

6. The method of claim 1, wherein determining the baby status comprises selecting the baby status from one of: a crying status, a whining status, a babbling status, a laughing status, or a non-baby status.

7. The method of claim 1, wherein determining the output action comprises adjusting a swing speed, adjusting a vibration intensity, or adjusting a sound output volume.

8. The method of claim 1, wherein the first sound input is a discrete segment of sound data or streaming sound data.

9. The method of claim 1, further comprising:
   determining that the baby status is a soothed baby status; and
   implementing a post-soothing device setting modification.

10. The method of claim 1, wherein the baby status is a first baby status and the output action is a first output action, the method further comprising:
   receiving a second sound input;
   processing the second sound input;
   determining a second baby status based at least in part on the second sound input;
   determining that the second baby status is different than the first baby status; and
   determining a second output action based at least in part on the second baby status.

11. The method of claim 1, further comprising:
detecting a motion of a baby; and
determining an amount of motion of the baby;
wherein determining the output action is based at least in part on the amount of motion of the baby.

12. An apparatus comprising:
a baby supporting portion; and
one or more processors configured to execute computer-executable instructions to:
receive a first sound input;
process the first sound input comprising:
determining a Fourier transform of the first sound input; and
determining a standard deviation of the Fourier transform;
determine a baby status based at least in part on the standard deviation of the Fourier transform; and
determine an output action based at least in part on the baby status.

13. The apparatus of claim 12, wherein the one or more processors is configured to determine the output action by adjusting a swing speed, adjusting a vibration intensity, or adjusting a sound output volume.

14. The apparatus of claim 12, wherein the baby status is a first baby status and the output action is a first output action, and wherein the one or more processors is further configured to:

receive a second sound input;
process the second sound input;
determine a second baby status based at least in part on the second sound input;
determine that the second baby status is different than the first sound input; and
determine a second output action based at least in part on the second baby status.

15. The apparatus of claim 12, further comprising at least one of: a swing apparatus, a vibration motor, one or more light sources, or one or more speakers.

16. The apparatus of claim 12, further comprising a motion sensor, wherein the one or more processors is further configured to:
detect a motion of a baby; and
determine an amount of motion of the baby;
wherein the controller is configured to determine the output action is based at least in part on the amount of motion of the baby.

17. The apparatus of claim 12, wherein the baby supporting portion is one of a swing or a rocker and the output action is one of adjusting a swing speed or adjusting a vibration intensity.

* * * * *